United States Patent
Cummings

[19]

[11] Patent Number: 6,138,312
[45] Date of Patent: Oct. 31, 2000

[54] SINGLE-USE CONTACT LENS TREATMENT APPARATUS

[76] Inventor: Eugene M. Cummings, 1290 Kathryn La., Lake Forest, Ill. 60045

[21] Appl. No.: 09/277,315

[22] Filed: Mar. 26, 1999

[51] Int. Cl.[7] .......................... G02C 13/00; B08B 11/00; A61L 12/00
[52] U.S. Cl. .................................. 15/104.92; 15/104.93; 15/214; 15/244.1; 206/5.1
[58] Field of Search .......................... 15/104.92, 104.93, 15/104.94, 214, 244.1; 206/5.1, 6, 207, 210, 438; 134/901

[56] References Cited

U.S. PATENT DOCUMENTS

| | | | |
|---|---|---|---|
| 1,003,761 | 9/1911 | Lehmann | 15/214 |
| 1,708,728 | 10/1929 | Kilbride | 15/214 |
| 2,906,643 | 9/1959 | Dennis | 15/244.4 X |
| 2,932,383 | 4/1960 | Fagan | 206/5.1 |
| 3,037,616 | 6/1962 | Phipps, III | 206/5.1 |
| 3,054,412 | 9/1962 | Nickell | 134/137 |
| 3,083,819 | 4/1963 | Entzminger | 206/5.1 |
| 3,089,500 | 5/1963 | Stalcup | 134/156 |
| 3,149,364 | 9/1964 | Baptist et al. | 15/104.94 |
| 3,344,461 | 10/1967 | Floor | 206/5.1 |
| 3,369,656 | 2/1968 | Skinner, Jr. | 206/205 |
| 3,377,643 | 4/1968 | Teng et al. | 15/118 |
| 3,871,395 | 3/1975 | Murry | 134/107 |
| 3,977,517 | 8/1976 | Kadelcik et al. | 206/5.1 |
| 3,990,579 | 11/1976 | Manning | 206/5.1 |
| 4,187,574 | 2/1980 | Wrue | 15/104.92 |
| 4,202,740 | 5/1980 | Stoner et al. | 205/701 |
| 4,480,352 | 11/1984 | Eggett | 15/214 |
| 4,493,783 | 1/1985 | Su et al. | 510/113 |
| 4,533,399 | 8/1985 | Mencke | 134/6 |
| 4,559,662 | 12/1985 | Kunold, Jr. | 15/104.94 |
| 4,613,379 | 9/1986 | Su et al. | 134/7 |
| 4,732,185 | 3/1988 | Cowle et al. | 204/267 |
| 4,792,414 | 12/1988 | Su et al. | 510/113 |

(List continued on next page.)

FOREIGN PATENT DOCUMENTS 0268087  10/1987  European Pat. Off. .
2061709  5/1981  United Kingdom .

OTHER PUBLICATIONS

"Identification Prevention and Removal of Contact Lens Deposits", (booklet) *Optometry Documents*, (1984).

"Protein Migration Through Hydrogels: A Tool for Measuring Porosity—Application to Hydrogels Used as Contact Lenses", by A. M. Gachon, et al. *Analyzed Biochemistry* (1968), pp. 249–255.

"Deposits on Soft Contact Lenses. Electrophoresis and Scanning Electron Microscopic Examination", by T. Bilbaut, et al. Exp. Eye Res, (1968), pp. 153–165.

"The Effect on Measured Visual Acuity of Protein Deposition and Removal in soft Contact Lenses", by David A. McClure, et al. *Contacto*, Mar. 1977, pp. 8–12.

"Cleaning Hydrophilic Contact Lenses: An Overview", by Stuart Ericksen, *Annals of Opthalmology*, Sep. 1975, pp. 1223–1232.

*Primary Examiner*—Mark Spisich
*Attorney, Agent, or Firm*—Cook, Alex, McFarron, Manzo, Cummings & Mehler, Ltd.

[57] ABSTRACT

A self-contained single-use apparatus for cleaning and hydrating a pair of contact lenses comprises a rigid base member. A first sponge member is contained in a first recess formed on a first portion of the base member. A second sponge member is contained in a second recess formed on a second portion of the base member. A thin layer of reactive material is deposited on the exposed face of each sponge member. A crease line on the base member allows the first base portion to be folded over the second base portion, whereby the layers of reactive material contiguously engage the optical surfaces of a lens disposed therebetween. In one embodiment the base member portions are held in engagement by an adhesive layer extending around the periphery of the base member. In another embodiment integrally formed tongs on the one portion of the base member engage eyelets on the other portion. A thin flexible layer of foil is adhesively bonded to the top surface of the rigid base member to seal the open ends of the recesses prior to use.

9 Claims, 4 Drawing Sheets

U.S. PATENT DOCUMENTS

| | | | |
|---|---|---|---|
| 4,839,082 | 6/1989 | Bhatia | 134/26 |
| 4,840,681 | 6/1989 | Pompe | 134/42 |
| 4,852,592 | 8/1989 | DiGangi et al. | 134/57 R |
| 4,872,965 | 10/1989 | Pankow | 204/468 |
| 5,017,238 | 5/1991 | Chromecek et al. | 134/7 |
| 5,037,484 | 8/1991 | Su et al. | 134/7 |
| 5,037,485 | 8/1991 | Chromecek et al. | 134/7 |
| 5,054,610 | 10/1991 | Ajello | 206/5.1 |
| 5,071,276 | 12/1991 | Nielson et al. | 401/9 |
| 5,073,202 | 12/1991 | Wallach | 134/6 |
| 5,100,477 | 3/1992 | Chromecek et al. | 134/7 |
| 5,114,686 | 5/1992 | Gillespie | 422/300 |
| 5,127,126 | 7/1992 | Tanaka et al. | 15/214 |
| 5,128,058 | 7/1992 | Ishii et al. | 510/113 |
| 5,227,039 | 7/1993 | Pankow | 204/551 |
| 5,368,708 | 11/1994 | Pankow | 205/688 |
| 5,439,572 | 8/1995 | Pankow | 204/450 |
| 5,529,678 | 6/1996 | Pankow | 204/600 |
| 5,657,506 | 8/1997 | Pankow | 15/104.92 |

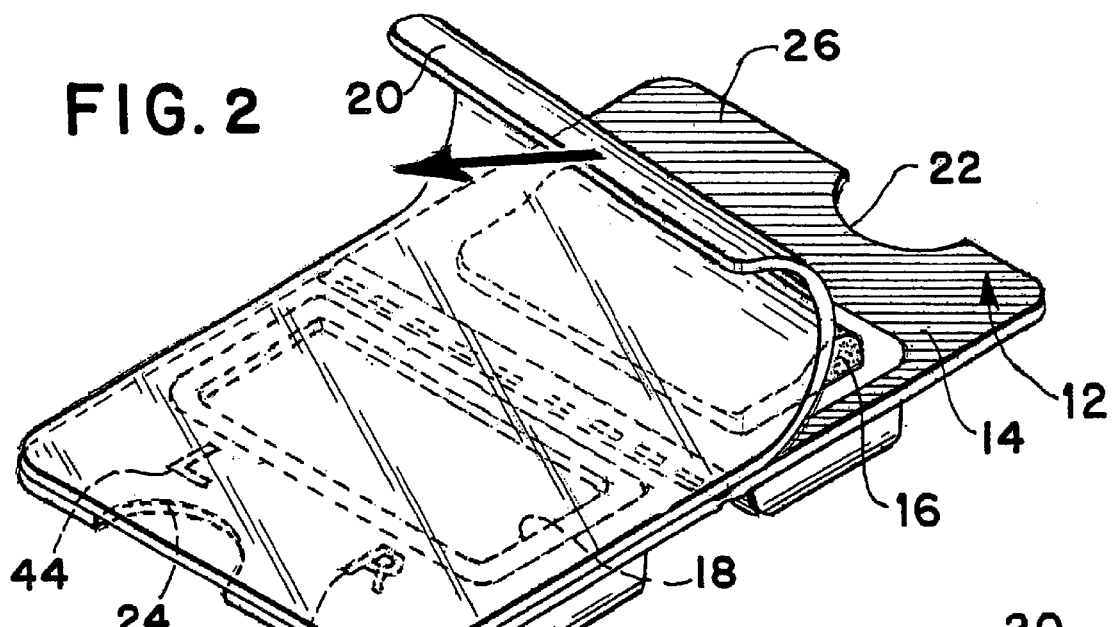
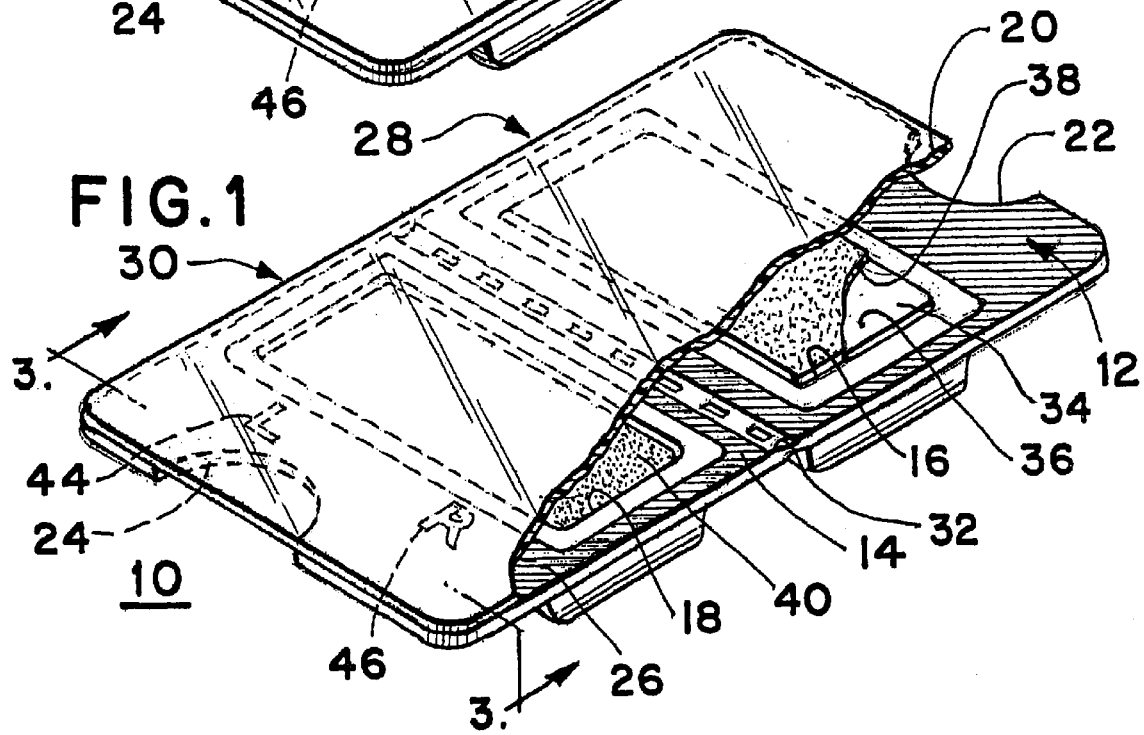
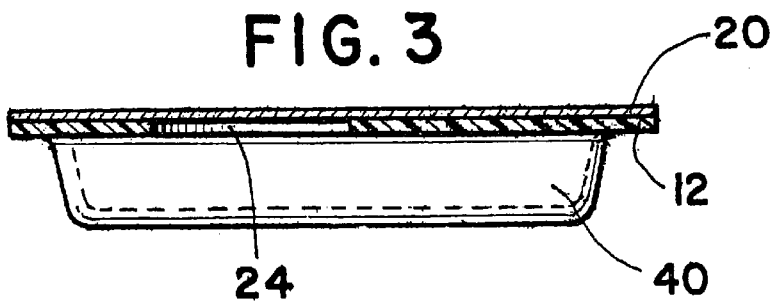

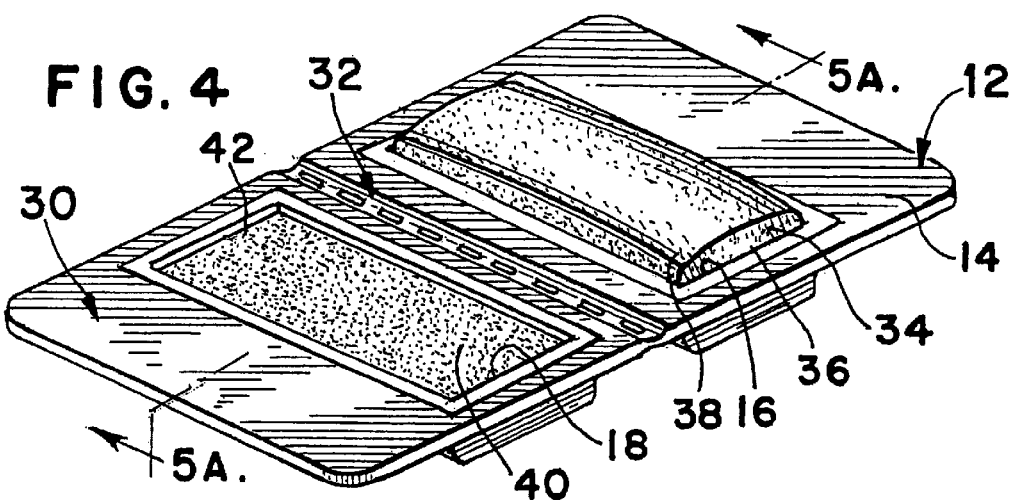
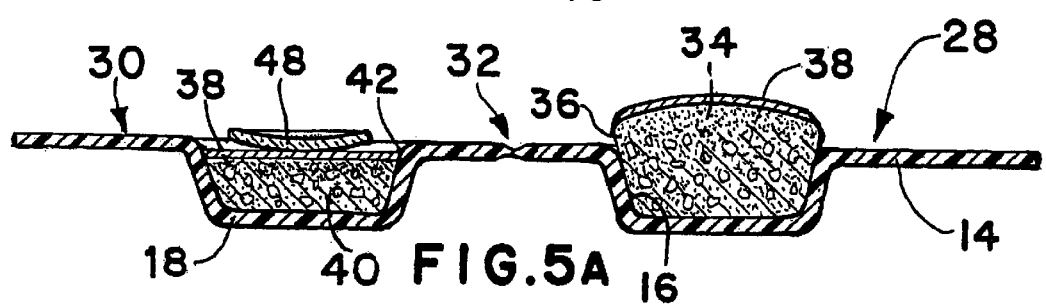
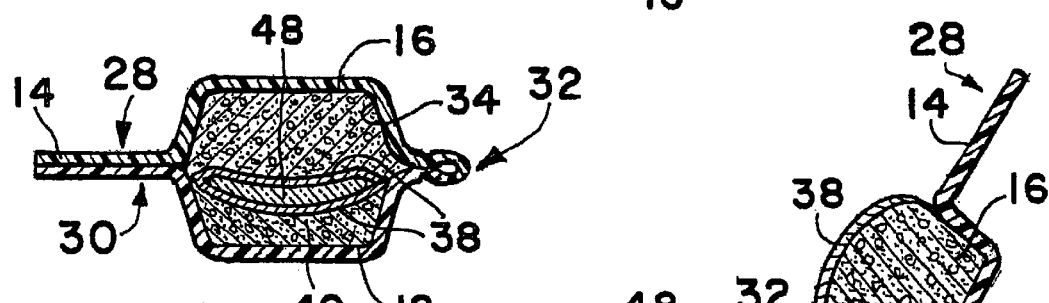
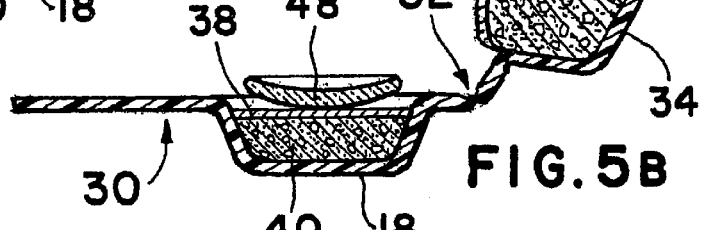
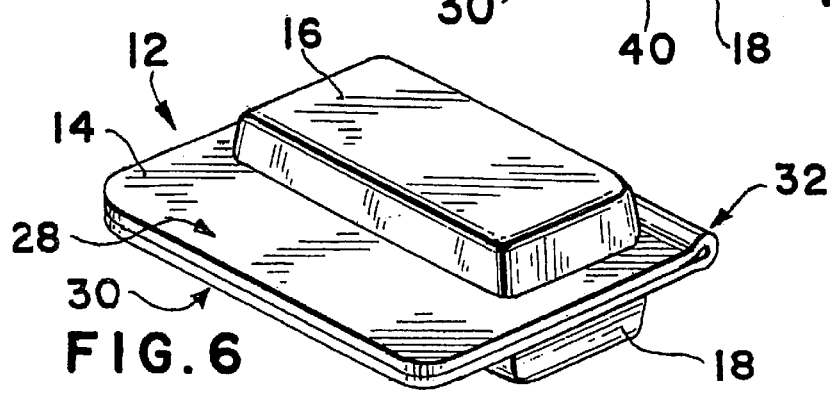

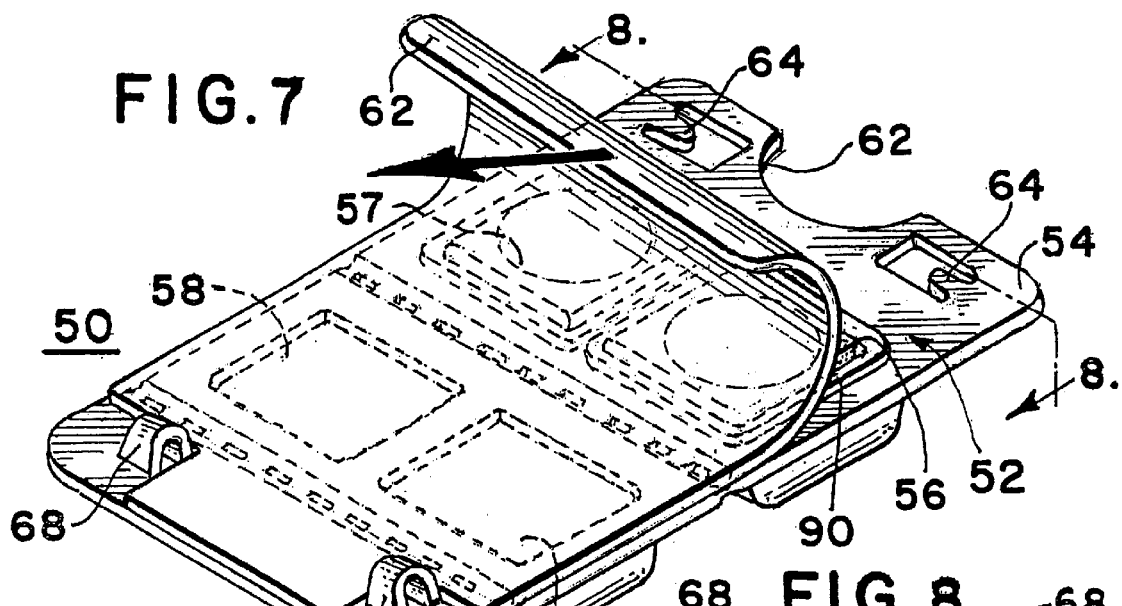
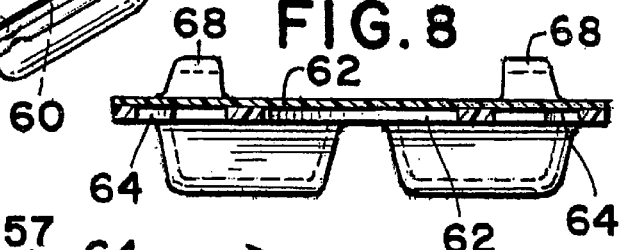
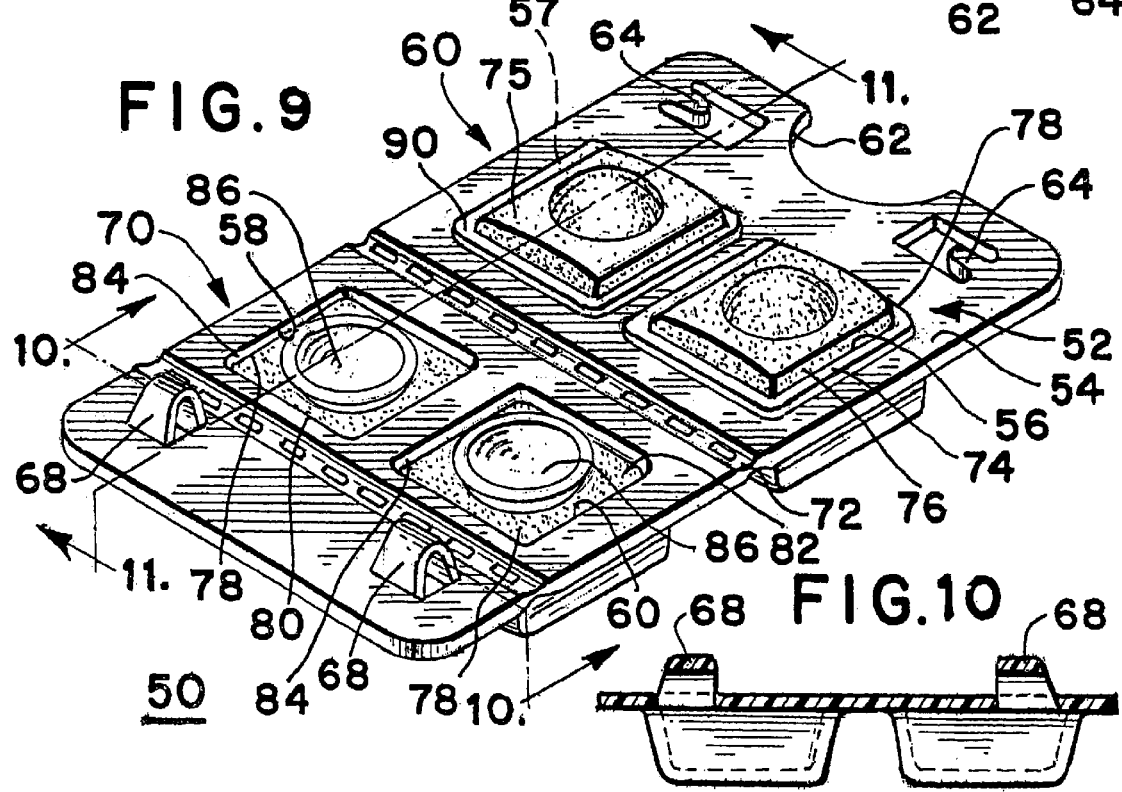

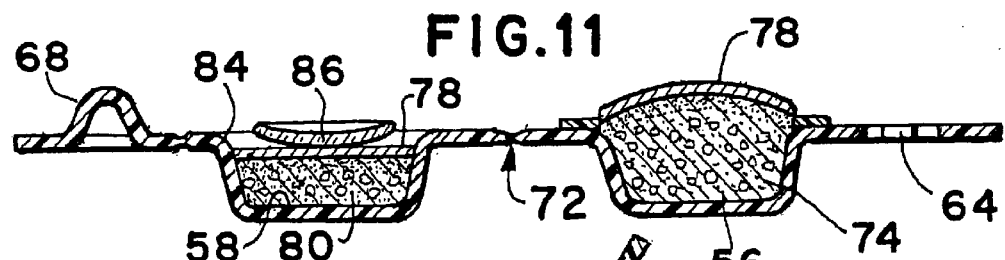
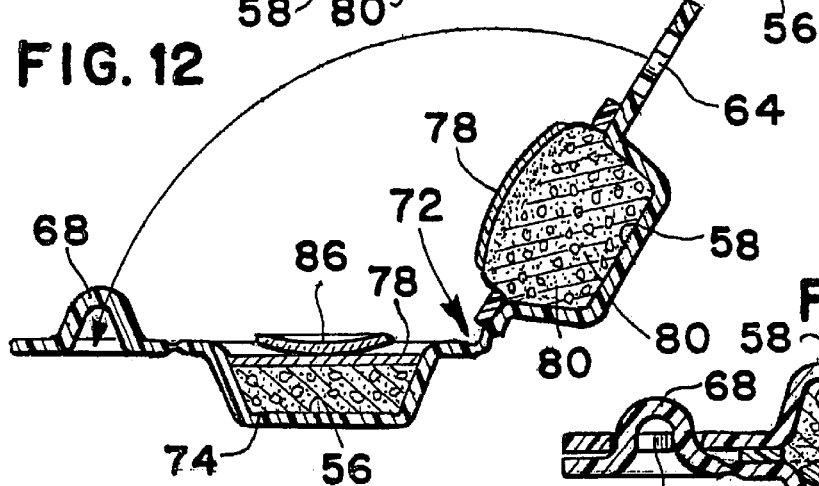
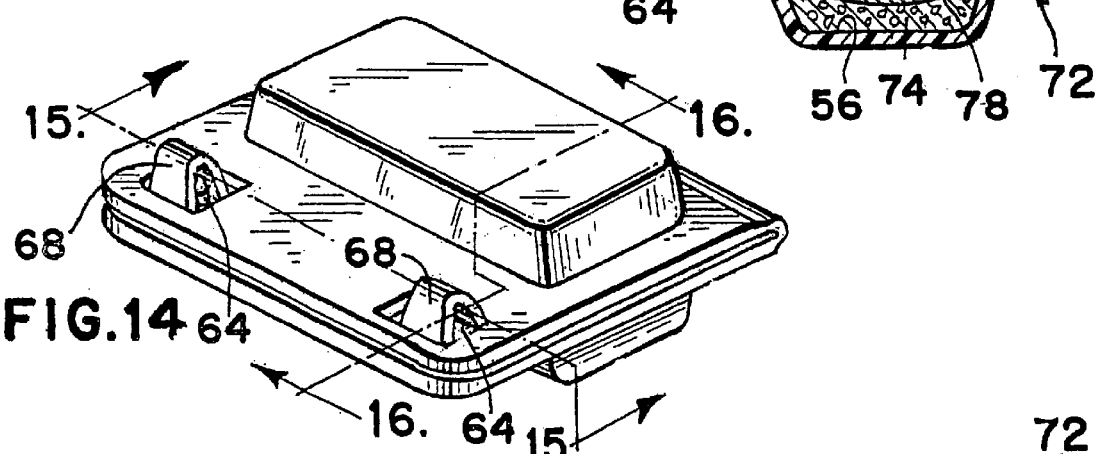
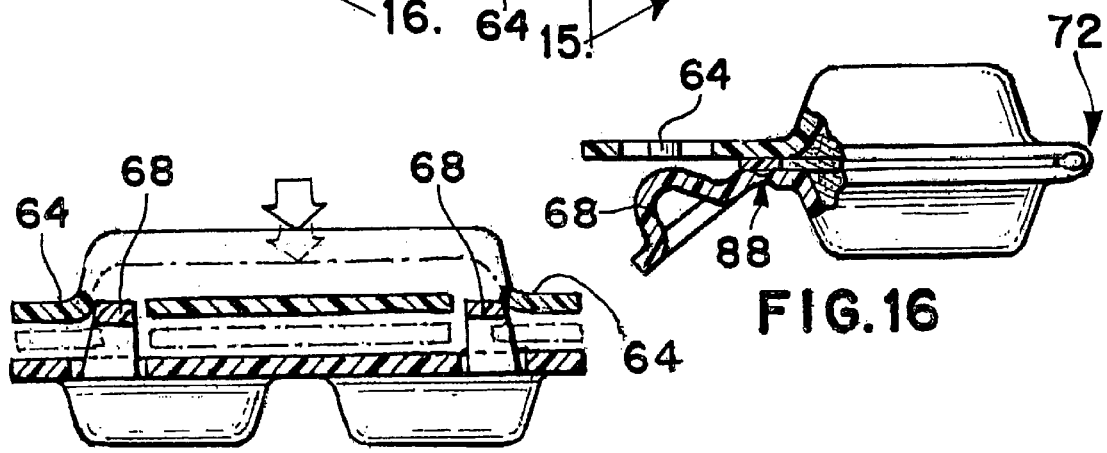

SINGLE-USE CONTACT LENS TREATMENT APPARATUS

BACKGROUND OF THE INVENTION

The present invention is directed to an apparatus for treating contact lenses. More particularly, the invention is directed to a stand-alone apparatus by which contact lenses can be cleaned and hydrated without the application of heat, mechanical agitation or cleaning chemicals to the lenses. The apparatus is single-use and disposable, and comprises a housing defining a pair of closeable liquid sealed lens containers within which the lenses are contained and brought into contiguous wetted contact with layers of reactive material during the treatment process.

Contact lenses have come into wide use for correcting a wide range of vision deficiencies or cosmetic use. Typically, such lenses are formed from a thin transparent plastic material shaped and dimensioned to fit over the cornea of the eye. The lenses include a concave interior first optical surface for contact with the eye, and an opposed and optically associated convex exterior second optical surface. The two surfaces together define a corrective lens medically prescribed for a particular eye.

Depending on the plastic material used to construct the lenses, the lenses may be either "hard" or "soft". Hard contact lenses, which are comparatively more rigid, are typically formed from a relatively hydrophobic material such as polymethylmethacrylate (PMMA). Soft contact lenses, which are comparatively more pliant, are typically formed from a relatively hydrophylic polymer such as hydroyethylmethacrylate (HEMA), which has the property of being able to absorb and bind a proportionately large amount of water within the polymer network. Soft contact lenses formed from such hydrophilic polymers, when hydrated, are more comfortable to wear than hard lenses because they better conform to the cornea of the eye and cause less irritation when worn for extended periods. For this reason, the great majority of contact lenses presently being prescribed are of the soft type.

Unfortunately, soft contact lenses while being worn may collect contaminants from the eye and its environment. These contaminants, for example, may include proteins and lipids from the tear fluid of the eye, and foreign substances such as cosmetics, soaps, airborne chemicals, dust and other particulate matter. Unless periodically removed, these contaminants may cause abrasion to the surface of the eye, may impair the visual acuity of the lens, and may serve as a nutrient media for potentially harmful microorganisms.

Furthermore, for wearing comfort it is necessary that soft contact lenses be maintained uniformly hydrated at all times. While on the eye, the moisture content of the hydrophilic material of the lenses is maintained by tear fluid. However, when the lenses are removed for an extended period, as for cleaning or while sleeping, the lenses may dry out and become irreversibly damaged unless they are externally hydrated.

Consequently, various apparatus and methods have been developed for cleaning and hydrating soft contact lenses. For example, cleaning apparatus has been provided wherein the lenses are submersed in a variety of liquid cleaning agents, such as surficants, oxidants, disinfectants, enzymatic cleaners, or abrasives. Other cleaning apparatus has been provided which included mechanically operated or electrically powered components for vibrating, rotating, abrading, scrubbing, heating, agitating, subjecting to ultrasonic energy, or otherwise mechanically manipulating the lenses to enhance the cleaning action of the cleaning agent.

Such prior apparatus have not been entirely satisfactory for various reasons, including lack of cleaning effectiveness with respect to certain of the various contaminants found on the lenses, undesirable complexity, excessive time required for use, and dependence on an external power source.

One apparatus which overcomes these shortcomings is described in U.S. Pat. No. 5,657,506. This apparatus utilizes a two-section lens container wherein the exposed surfaces of two sponge members, wetted with an ophthalmologically-compatible solution, and each having thereon a reactive layer formed of a highly porous non-abrasive relatively polymeric material such as polytetrafluoroethylene (PTFE), are brought into compressive engagement with the optical surfaces of an interposed contact lens whereby the reactive layers cause contaminants to migrate from the lens to the reactive layers.

The present invention is directed to an alternative housing construction from that described in the above-identified patent which is simpler to use and which can be more economically manufactured for single-use and disposal.

Accordingly, it is a general object of the present invention to provide a new and improved apparatus for cleaning contaminated contact lenses.

It is a more specific object of the invention to provide an apparatus for cleaning contaminated contact lenses which is simpler to use and more economical to manufacture.

It is a further object of the present invention to provide an improved disposable single-use apparatus for cleaning contaminated contact lenses wherein a rigid base member having recesses thereon is folded to form liquid-sealed chambers for containing the lenses while the lenses are being cleaned.

It is a further object of the invention to provide an improved self-contained apparatus for cleaning contaminated contact lenses wherein recesses containing a sponge members coated with a reactive material are provided on a rigid base member such that when the base member is folded chambers are formed wherein the optical surfaces of the lenses are received in a wetted environment in contiguous contact with the reactive layers and contaminants are attracted away from the lenses.

SUMMARY OF THE INVENTION

The invention is directed to a contact lens cleaning apparatus for cleaning contact lenses of the type having generally opposed optical surfaces, comprising a generally rigid base member having a first portion and a second portion, a first recess forming a first open-ended chamber on a top surface of the first base portion, a second recess forming a second open-ended chamber on the top surface of the second base portion, a removable cover member extending over the top surface of the base portion to close the chambers, the first and second base portions being connected by a hinge portion enabling the second base portion to be folded over on the first base portion with the open ends of the chambers in general alignment, a first compressible sponge member disposed in the first chamber and having an operative face facing the open end of the first chamber, a second compressible sponge member disposed in the second chamber and having an operative face facing the open end of the second chamber, the sponge member being wetted with an ophthalmologically compatible solution, a portion of each of the operative faces each including a reactive layer, the operative sponge faces coming into compressive engagement when the second base portion is folded over the first base portion whereby the reactive surfaces come into engagement with respective optical surfaces of a lens positioned therebetween, and means for securing the second base portion in the folded over position to enable contaminants to transfer from the lens to the reactive surfaces.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a contact lens treatment apparatus constructed in accordance with the invention in a sealed condition prior to use.

FIG. 2 is a perspective view of the contact lens treatment apparatus of FIG. 1 showing the cover member partially peeled away.

FIG. 3 is a cross-sectional view of the contact lens treatment apparatus of FIG. 1 taken along line 3—3 of FIG. 1.

FIG. 4 is a perspective view of the contact lens treatment apparatus of FIGS. 1–3 showing the lens containers thereof open for receiving a pair of conventional soft contact lenses for treatment.

FIG. 5A is an enlarged cross-sectional view of the contact lens cleaning apparatus of FIG. 4 in an open condition.

FIG. 5B is a cross-sectional view similar to FIG. 5A showing the lens cleaning apparatus in a partially closed position.

FIG. 5C is a cross-sectional view similar to FIG. 5A showing the lens cleaning apparatus in a closed condition.

FIG. 6 is a perspective view of the lens cleaning apparatus in a closed condition.

FIG. 7 is a perspective view of an alternative embodiment of the lens cleaning apparatus of the invention.

FIG. 8 is a cross-sectional view of the lens cleaning apparatus of FIG. 7 taken along lines 8—8 of FIG. 7.

FIG. 9 is a perspective view of the base member of the lens cleaning apparatus of FIGS. 7 and 8 with the cover removed.

FIG. 10 is a cross-sectional view of the lens cleaning apparatus of FIGS. 7–9 taken along lines 10—10 of FIG. 9.

FIG. 11 is a cross-sectional view of the lens cleaning apparatus of FIGS. 7–10 taken along lines 11 of FIG. 9.

FIG. 12 is a cross-sectional view similar to FIG. 11 with the base member partially folded.

FIG. 13 is a cross-sectional view similar to FIG. 11 with the base member folded.

FIG. 14 is a perspective view of the lens cleaning apparatus of FIGS. 7–13 in a closed position.

FIG. 15 is a cross-sectional view taken along lines 15—15 of FIG. 14 showing the locking tines engaging the tine engaging apertures of the base member.

FIG. 16 is a side elevational view partially in section showing the latch mechanism of the lens cleaning apparatus of FIGS. 7–15 being opened prior to removal of the contact lenses.

DESCRIPTION OF THE PREFERRED EMBODIMENTS

Referring to the Figures, and particularly to FIGS. 1–6, a lens treatment apparatus 10 constructed in accordance with the invention is seen to include a relatively rigid base member 12 having a top surface 14 on which two recesses or chambers 16 and 18 are formed. A thin layer 20 of non-porous material, such as metal foil, is attached to the base member 12 around its periphery by a peripheral strip of adhesive or the like. Prior to use the foil is peeled away, as shown in FIG. 2, to expose the open ends of chambers 16 and 18. A pair of thumb recesses 22 and 24 may be provided at respective ends of the base member 12 to facilitate removal of the foil and subsequent separation of the body sections when folded over to engage each other. A layer of adhesive 26 is disposed on top surface 14 to hold the body sections tightly closed when the second body section 28 is folded over the first body section 30 along the hinged portion or fold line 32. The fold line 32 of the present invention is designed for single use only, such that before use, the first and second body sections 30 and 28 are held relatively rigidly and in generally the same plane. When the second body section 28 is folded over the first 30 (FIGS. 5B and 5C), the fold line 32 collapses and losses its rigid property to become a flexible hinge thereby enabling the second and first body sections to come into contact with one another as shown in FIG. 6.

As shown in FIG. 4, a sponge 34 is positioned in chamber 16, preferably with an exposed surface 36 projecting through the open end of the chamber. A thin layer of reactive material 38 covers surface 36 to provide for cleaning one of the optical surfaces of the lens. Cooperating sponge 40 is positioned in chamber 18, preferably in a recessed manner leaving an exposed portion 42 of chamber 18. A thin layer of reactive material 38 similarly covers sponge 40 to provide for cleaning the other optical surface of the lens.

The present invention preferably includes identification means shown as a raised "L" 44 and a raised "R" 46 embossed on the top surface 14 of the first body section 30 to facilitate ready identification of the left and right lens of the user, even if vision-impaired. Alternatively, the lenses may be distinguishable through a separation of each of the chambers 16 and 18, as shown in FIGS. 7–10, to form separate chambers for the left and the right lenses of a user. If four chambers are utilized, then it will be understood that the same materials and relationships previously discussed apply.

Referring to FIGS. 5A–5C, sponge 34 is seen to comprise a relatively thick and porous material dimensioned to fit snugly within chamber 16 and formed with a generally concave surface over which a thin reactive layer of a reactive material 38 is provided to form a concave lens engaging surface. Similarly, sponge 40 is seen to comprise a relatively thick and porous material dimensioned to fit snugly within chamber 18 and formed with a generally convex surface over which a thin reactive layer of a reactive material 38 is provided to form a cooperating convex lens engaging surface.

During use, the user removes his contact lenses 48 and places them on the reactive layer 38 of the first body section 30 (FIG. 5A). The second body section 28 is then folded over the first body section 30 along hinged portion 32 as shown in FIG. 5B. As shown in FIG. 5C, when the apparatus 10 is closed the reactive surfaces 38 of the first and second body sections are brought into contiguous engagement of the optical surfaces of the lens 48. The exposed surface 36 of sponge 34 is preferably dimensioned slightly oversized with respect to the exposed portion 42 of chamber 18, so that as the second and first body sections come together the layers are slightly compressed to provide a conforming contiguous contact between the optical surfaces of the lenses and the respective contacting reactive layer surfaces. After an appropriate amount of time has lapsed, the two body sections are separated by pulling apart the contacting adhesive layers 26 via recesses 22 and 24.

During the manufacture of the apparatus 10, sponges 34 and 40 are preferably moistened with an ophthalmologically compatible solution. When contact lens 48 is inserted in the apparatus for cleaning (as shown in FIG. 5A), and the apparatus is subsequently folded over by the user (as shown in FIGS. 5B and 5C), the accompanying compression of sponges 34 and 40 causes solution absorbed therein to flow around the ends of the reactive layers 38 and around over and under lens 48, providing a fluid layer between the optical surfaces of the lenses and the contiguous contacting surfaces of reactive layers 38, respectively.

Reactive layers 38 may, for example, be formed from a material which is hydrophobic relative to the relatively hydrophylic material of lens 48 and which has an average pore size slightly less than that of the protein contaminants of the lens. Consequently, when the optical surfaces of the lens are brought into wetted contiguous contact with the surface of these layers, lipids and other protein contaminants attached to the lens migrate from the lens surface to the surfaces of the reactive layers, and remains there when the lens is removed. This occurs on both the convex and the concave surfaces of the lens. The contaminants being attracted to the adjacent reactive layers by reason of the natural migration of hydrophobic proteins and lipids and other contaminants from a less hydrophobic environment (the lens surface) to a more hydrophobic environment (the reactive layer surface) through the opthalmologically-compatible solution.

For optimum migration it is desirable that the reactive layer conforms to the surface of the lens. To this end reactive layers 38 are preferably thin and flexible, and deformable by their associated compressible sponge layers 34 and 40 to the optical surfaces of the lens. The reactive layers 38 may be joined to the sponge layers by known techniques such as vapor deposition or spraying of the reactive material over the relatively more porous surface of the underlying compressible layer.

It is preferable that chambers 16 and 18 each have sufficient interior volume to enable an adequate volume of ophthalmologically-compatible solution to be absorbed in the compressible layers of each to maintain the lens wetted during processing. Leakage and evaporation of the ophthalmologically-compatible solution is prevented during treatment of the lenses by adhesive 26, which holds the body sections tightly closed when folded upon each other. The seal provided by foil package 20 prevents evaporation of the ophthalmologically-compatible solution before use and during any long term storage.

The compressible sponge layers 34 and 40 are preferably formed from a highly porous absorbent material which accepts and retains moisture within its porous structure, and has an appreciable moisture content and therefore does not generally require re-wetting prior to use. Inert foraminous materials such as reticulated foams and papers are preferred materials for this purpose. Preferred ophthalmologically-compatible solutions for wetting the compressible layers include those known ophthalmologically-compatible solutions such as sold by Bausch & Lomb, Alcon, Giba-Geigy, and Allergan. The solutions may contain ophthalmologically-compatible anti-microbial agents or preservatives.

The reactive layer may be formed from a highly porous non-abrasive relatively polymeric material such as polytetrafluoroethylene (PTFE), polyvinylidene fluoride (PVDF), polypropylene, polyethylene, polyacrylonitrile, polymethylmethacrylate, polysulfone, polycarbonate, or cellulose acetate. PFTE is commercially available from W. L. Gore & Associates, Inc. PVDF is commercially available from the Millipore Corporation.

Polymers which exhibit a charged surface to which contaminants are attracted are suitable for use in the reactive layers, and include certain cellulosics, polyamides, and nylon-based compositions, such as those commercially available from the Pall Corporation.

Other suitable reactive materials are those that have been altered such chemical linkage occurs between the reactive material and reactive chemical groups found on proteins and other biological macromolecules contaminating the lens. The actual active group or groups that result in a covalent chemical linkage may depend on the pH of the surrounding fluid. "IMMUNODYNE", a product of the Pall Corporation is a commercially available example of one such material.

The attraction of lens contaminants to the reactive layer is the result of multiple forces and reactions which result in a greater net force being exerted between the reactive material and the contaminant than between the lens material and the contaminant. The forces include physicochemical forces, such as hydrophobic interactions at the molecular level which result from non-polar substances attracting other non-polar substances in the presence of more polar molecules such as water. Other molecular forces, such as Brownian motion or simple diffusion, and other attractive forces, such as London-van der Waals forces, may also contribute to the migration.

Furthermore, it has been found that those compositions that typically contaminate a lens are, after being drawn off the lens to the reactive material, adsorptively sequestered onto the reactive layer. The adsorptive sequestration of the contaminants may be due, in part, to the net electric charge of the contaminant and the opposite electric charge of the reactive material. The net charge varies with the type of contaminant and the composition and pH of the moisture or fluid that surrounds the contaminant.

The surface configuration of the reactive material may be varied in size and shape to optimize the performance of the reactive material and thereby the performance of the treatment apparatus. Material including pores of only a relatively large diameter advantageously is able to accommodate contaminants both of a large size and a wide range of smaller sizes. However, as the diameter of the pores increases, the pore surface area, and hence the adsorptive capacity of the material, decreases. Reactive material including pores having a wide range of diameters and including pores of smaller sizes will have a greater pore surface area and thereby greater adsorptive capacity (compared to a material having pores of only a larger diameter). To draw and retain the largest percentage of contaminants from a lens, the pore diameter of the reactive material preferably is within the range of approximately 0.1 micron to approximately 2 microns. A reactive material including pores having diameters that approximate the size of the contaminants drawn from the lens is advantageous in that it lessens the likelihood that any contaminants can pass through the reactive material without being adsorbed onto the walls of the reactive material. A reactive material having pores ranging in size from 0.1 micron to 0.5 micron will adsorb on the surface and within the porous structure of the material contaminants having molecular weights of between 1 thousand to 1 million daltons.

The pores of the reactive material may be varied in shape in order to optimize the performance of the treatment apparatus. Materials having pore sizes that are tortuous, irregularly shaped and generally of long length advantageously have a larger surface area-to-volume ratio than materials with regular shaped, shallow pores. Moreover, the amount of active surface of the material in close proximity to the lens is increased, thereby increasing the likelihood of rapid adsorption of contaminants onto the surface of the reactive material.

The pores of the reactive layer may also be varied in distribution through the reactive layer to optimize the performance of the treatment apparatus. For example, a reactive layer may have pores of a larger size at or near the surface on which the lens is positioned. In this case, the contaminants that are generally of a larger size will be selectively retained near the surface while contaminants that are generally of a smaller size will be retained within the material at a depth away from the surface.

A further understanding of the invention can be obtained by reference to the following description of an evaluation conducted with respect to a conventional commercially available soft lens and the removal of compositions coated on the lens. This description is provided for purposes of illustration only and is not included to be limiting unless otherwise indicated.

Johnson & Johnson "ACUVUE" soft lenses were sectioned and immersed in test tubes containing artificial tear solution comprising 1.2 mg/ml egg white lysozyme, 3.9 mg/ml of bovine serum albumin, and 1.6 mg/ml of gamma globulin in a citric acid phosphate isotonic buffer solution. To ensure that each lens was coated with protein, the test tubes containing the lenses were shaken for 2 hours at room temperature. The sectioned lenses were removed and inspected. Generally, the lenses had a filmy appearance. Each of the lenses was placed in 2 milliliters of physiological saline solution and mixed for 10 seconds to remove any unbound protein. The rinsing step was repeated twice.

Each of the lenses was then individually positioned on a surface of reactive material. specifically, the reactive material comprised a thin layer of PVDF moistened with a physiological saline solution. The lenses were allowed to remain positioned in contact with the material for various periods of time, after which each lens was removed from the material and inspected. Generally, the filmy appearance of the lens had decreased depending on the length of time the lens was allowed to remain in contact with the material.

To determine to what extent the contaminants had been removed from the lens by the reactive material, the reactive material was first allowed to air dry. Subsequently, the material was immersed in a standing solution of Commassie brilliant blue comprising 0.2% Commassie brilliant blue in 50% methanol and 10% acetic acid. Commassie brilliant blue stained those portions of the reactive material that had adsorbed protein. The reactive material was removed from the stain and washed with a solution comprising 22.5% methanol and 3.5% acetic acid to remove any stain not bound to compositions on the material. Each of the material sections showed a distinct blue staining generally corresponding to the outline of the corresponding sectioned lens.

A pair of lenses may be advantageously treated using the apparatus of the present invention as follows. First, the foil cover 20 is removed to expose chambers 16 and 18 and the reactive surfaces therein. Then, the lenses are removed and positioned on the pre-wetted reactive surfaces. The two lens containers are then closed, causing the optical surfaces of the lenses to be brought into contiguous wetted contact with the reactive surfaces of the apparatus. The lenses are allowed to remain in the closed containers for a period of time proportional to the degree to which the lenses are contaminated and/or the length of time since the lenses were last cleaned. Generally, a significant amount of contaminants are dislodged from contaminated-coated lenses that remain in the housing for a period of 2 hours. Heavily contaminated lenses may require a longer period of time, such as overnight when the wearer is sleeping. After the treatment has been accomplished, the lenses are removed from the apparatus and returned to the user's eyes. The treatment apparatus, now containing the contaminants, may be appropriately disposed.

An alternate embodiment of the present invention is providing separate chambers for the left and right contact lenses and a snap closure described in FIGS. 7–16. It will be understood that except for the additional chambers and the snap closure the manufacture, dimensions, materials, reactions, etc. of this alternate embodiment is as previously discussed. Similar to the previously-described embodiment, the alternate embodiment of lens treatment apparatus 50 includes a relatively rigid base member 52 having a top surface 54 on which four recesses or chambers 56, 57, 58 and 60 are formed. A thin layer 62 of non-porous material, such as metal foil, is attached to the base member 52 around its periphery by a peripheral strip of adhesive or the like. Prior to use the foil is peeled away, as shown in FIG. 7, to expose the open ends of chambers 56, 57, 58 and 60. A thumb recess 62 may be provided at an end of the base member 52 to facilitate removal of the foil and subsequent separation of the body sections when folded over to engage each other. A pair of locking tongs 64 are located on the second body section 66 to engage a pair of cooperating eyelets 68 located on the first body section 70 thereby holding/locking the body sections tightly closed when the second body section 66 is folded over the first body section 70 along fold line 72. Like fold line 32, fold line 72 is designed for single use only. Before use, the first and second body sections 70 and 66 are held relatively rigidly and in generally the same plane. When the second body section 66 is folded over the first 70 (FIGS. 12 and 13), fold line 72 creases and loses its rigid property to become a flexible hinge, enabling the second and first body sections to come into contact with one another as shown in FIG. 14.

As shown in FIG. 9, sponge members 74 and 75 are positioned in chambers 56 and 57, preferably with exposed surfaces 76 projecting through the open ends of the chambers. Thin layers 78 of reactive material cover surfaces 76 to provide for cleaning one optical surface of each lens. Cooperating sponges 80 and 82 are positioned in chambers 58 and 60 respectively, preferably with a recessed surface to provide separate recesses 84 in which the left and right lenses 86 can be conveniently deposited by the user. Thin layer 78 of reactive material cover sponges 80 and 82 to provide for cleaning the remaining optical surfaces of the two lenses.

Identification means such as a raised "L" and "R" embossed on the top surface of the second body section may be provided.

Referring to FIGS. 11–13, sponges 74 and 75 are seen to comprise a relatively thick and porous material formed to fit snugly within chamber 56 and 57 and are formed with a generally concave surface over which a thin layer of reactive material 78 is provided to form a concave lens engaging surface. Similarly, sponge 80 and 82 are seen to comprise a relatively thick and porous material dimensioned to fit snugly within chambers 58 and 60 and are formed with a generally convex surface over which a thin layer of a reactive material 78 is provided to form a convex lens engaging surface.

During use, the user removes his contact lenses 86 and places them on the reactive layers of sponges 80 and 82 (FIG. 11). The second body section 66 is then folded over the first body section 70 along hinged portion 72 as shown in FIG. 12. As shown in FIG. 13, when the apparatus 50 is closed reactive surfaces 78 of the first and second body sections are brought into contiguous engagement of the optical surfaces of the lens 86. The exposed surface 76 of sponge is preferably dimensioned slightly oversized with respect to the exposed portion 84 of chambers 56 and 58, so that as the second and first body sections come together, and tongs 64 lock with eyelets 68, the layers are slightly compressed to provide a conforming contiguous contact between the optical surfaces of the lenses and the respective contacting reactive layer surfaces. Leakage and evaporation of the ophthalmologically-compatible solution is prevented during treatment of the lenses by raised rim portions 90 on the base member, which provides a tight seal around the lens chambers when the body sections are folded over and locked to each other. After an appropriate amount of time has lapsed, the two body sections are separated by pulling apart the cooperating tongs 64 and eyelets 68 by use of thumb recess 62. Tongs 64 may be formed to break off when the eyelets are separated to discourage reuse of the apparatus.

While particular embodiments of the invention have been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A contact lens cleaning apparatus for cleaning contact lenses of the type having generally opposed optical surfaces, comprising:

a generally rigid base member having a first portion and a second portion;

a first recess forming a first open-ended chamber on a top surface of said first base portion;

a second recess forming a second open-ended chamber on said top surface of second base portion;

a removable cover member extending over said top surface of said base portions to close said chambers;

said first and second base portions being connected by a hinge portion enabling said second base portion to be folded over on said first base portion with said open ends of said chambers in general alignment;

a first compressible sponge member disposed in said first chamber and having an operative face facing said open end of said first chamber;

a second compressible sponge member disposed in said second chamber and having an operative face facing said open end of said second chamber;

said sponge members being wetted with an ophthalmologically compatible solution;

a portion of each of said operative faces each including a reactive layer;

said operative sponge faces coming into compressive engagement when said second base portion is folded over said first base portion whereby said reactive layers come into engagement with respective optical surfaces of a lens positioned therebetween; and means for securing said second base portion in said folded over position to enable contaminants to transfer from said lens to said reactive layers.

2. A contact lens cleaning apparatus as defined in claim 1 wherein said hinge portion of said base member comprises a portion of said base member having a reduced thickness relative to said first and second base portions.

3. A contact lens cleaning apparatus as defined in claim 2 wherein said hinge portion at least partially fractures upon said second base portion being folded back on said first base portion.

4. A contact lens cleaning apparatus as defined in claim 1 wherein each said reactive layer is formed of a hydrophilic material.

5. A contact lens cleaning apparatus as defined in claim 1 wherein said removable cover member is thin and flexible relative to said base member.

6. A contact lens cleaning apparatus as defined in claim 1 wherein said ophthalmologically compatible solution is a saline solution.

7. A contact lens cleaning apparatus as defined in claim 1 for cleaning a pair of contact lenses wherein said base member includes a first pair of recesses in said first portion each having a compressible sponge member disposed therein and a second pair of recesses in said second portion each having a compressible sponge member therein, said sponge members each having a reactive layer on the outside surface thereof, said recesses being arranged whereby when said second portion of said base member is folded over on said first portion of said base member said recesses form first and second chambers for receiving respective ones of said pair of contact lenses.

8. A contact lens cleaning apparatus as defined in claim 7 wherein said hinge portion of said base member comprises a portion of said base member having a reduced thickness relative to said first and second base portions.

9. A contact lens cleaning apparatus as defined in claim 8 wherein said hinge portion at least partially fractures upon said second base portion being folded back on said first base portion.

* * * * *